United States Patent [19]

Merrifield et al.

[11] Patent Number: 5,143,902
[45] Date of Patent: Sep. 1, 1992

[54] GLUCAGON ANALOGS WITH ASP⁹ REPLACEMENTS OR DELETIONS

[75] Inventors: Robert B. Merrifield, Creskill, N.J.; Cecilia G. Unson, New York, N.Y.

[73] Assignee: The Rockefeller University

[21] Appl. No.: 807,644

[22] Filed: Dec. 16, 1991

Related U.S. Application Data

[63] Continuation of Ser. No. 575,970, Aug. 31, 1990, abandoned.

[51] Int. Cl.⁵ .................... A61K 37/28; C07K 7/10; C07K 7/34
[52] U.S. Cl. ...................... 514/12; 530/308; 530/324
[58] Field of Search .................. 514/12; 530/308, 324

[56] References Cited

U.S. PATENT DOCUMENTS 4,879,273 11/1989 Merrifield .................... 530/308

OTHER PUBLICATIONS

Jour. of Bio. Chem. vol. 259, issue on Jun. 10, pp. 7031–7037, 1984, Semisynthetic Derivatives of Glucagon, Flanders, et al.

Primary Examiner—Merrell C. Cashion, Jr.
Assistant Examiner—S. G. Marshall
Attorney, Agent, or Firm—Henry T. Burke

[57] ABSTRACT

Glucagon analogs characterized principally by the removal of the 9-aspartic acid residue or its replacement with an amino acid residue other than an L- dibasic amino acid containing up to five carbon atoms with or without a histidine at the amino terminal are useful adjuncts to insulin therapy.

18 Claims, No Drawings

GLUCAGON ANALOGS WITH ASP[9] REPLACEMENTS OR DELETIONS

This invention was made with Government support under AI-11822 awarded by the National Institutes of Health. The Government has certain rights in this invention.

This application is a continuation application of copending application Ser. No. 07/575,970, filed Aug. 31, 1990, now abandoned.

BACKGROUND OF THE INVENTION

Glucagon is a 29-residue peptide hormone that regulates glycogenolysis and glucogenesis. The structure of glucagon may be represented as follows:

His—Ser—Gln—Gly—Thr—Phe—Thr—Ser—Asp—Tyr—Ser—Lys—Tyr—Leu—
1    2    3    4    5    6    7    8    9    10   11   12   13   14

Asp—Ser—Arg—Arg—Ala—Gln—Asp—Phe—Val—Gln—Trp—Leu—Met—Asn—Thr
15   16   17   18   19   20   21   22   23   24   25   26   27   28   29

The abbreviations utilized herein are those recommended by IUPAC-IUB [see Eur. J. Biochem. 138, 9 (1984)].

The nomenclature used to define the peptides is that specified by Schroder & Lubke, "The Peptides", Academic Press (1965), wherein in accordance with conventional representation the amino group at the N-terminal appears to the left and the carboxyl group at the C-terminal to the right. Where the amino acid residue has isomeric forms, it is the L- or naturally occurring form of the amino acid that is represented unless otherwise expressly indicated.

Insulin, as is known, rapidly decreases elevated blood sugar.

It is believed that, in humans, diabetes is only observed when insulin levels are low and glucagon levels are simultaneously elevated. The absence of insulin allows blood glucose to rise particularly after a meal, and the presence of glucagon causes a further rise in blood glucose. Large amounts of insulin are required to reduce the glucose levels to normal. The maintenance of stable levels is difficult and subject to considerable fluctuation. This wide fluctuation is responsible, at least in part, for the clinical difficulties experienced in diabetes.

Glucagon appears to act by binding to liver membrane receptors thereby activating adenylate cyclase which, in turn, triggers a series of reactions including the production of cyclic adenosine monophosphate (cAMP), which activates phosphorylase and inhibits glycogen synthetase, thereby contributing to elevated glucose levels in the blood.

Recently considerable effort has been expended to develop glucagon antagonists that will bind to the liver membrane but do not have the ability to transduce the signal to activate adenylate cyclase. One such product is Nα- trinitrophenyl [12-homoarginine] glucagon. This product does bind to the glucagon receptor without significant activation of adenylate cyclase. Unfortunately it activates another binding system in the hepatocyte membrane leading to the production of inositol trisphosphate and calcium ions. A useful antagonist will block the action of endogenous glucagon by preventing it from binding to the liver membrane receptors and thereby producing cAMP and glucose in the cell, and the ultimate elevation of blood sugar. Such products would be useful to reduce a diabetic's need for injections or infusion of insulin.

An ideal glucagon antagonist would (1) be completely inactive toward stimulation of adenylate cyclase and production of cAMP, (2) bind as well as glucagon itself to the liver membrane, (3) compete with glucagon for binding to the membrane, (4) at moderate concentrations fully inhibit the action of glucagon toward the activation of adenylate cyclase, and (5) have a satisfactory inhibition index.

The inhibition index is the molar ratio of antagonist to agonist which reduces the biological response to one half of the value for the agonist in the absence of antagonist. It will be discussed more fully hereinafter.

THE INVENTION

A class of glucagon antagonists has now been discovered which substantially fulfills the above criteria and does so with minimum side effects. The class is characterized by the deletion or replacement of the L-aspartic acid residue at the 9-position.

The compounds of this invention are best visualized as analogs of glucagon or derivatives thereof, such as amides characterized by the removal of the 9-aspartic acid residue or its replacement with an amino acid residue other than an L- dibasic amino acid containing up to 5 carbon atoms.

The replacement acid residue for the 9-aspartic acid moiety can be selected from amongst any of the L- and D-form amino acids, both naturally occurring and synthetic, including hydrophobic and hydrophilic amino acids, aliphatic amino acids, aryl amino acids, basic amino acids and acidic amino acids, containing more than 5 carbon atoms. One or more of the other amino acid residues in the glucagon chain may be removed or replaced, but the key to optimum utility appears to be removal or replacement of the 9-aspartic acid residue.

Compounds of the invention may be represented by the notations:

---
Leu[5] Lys[9] glucagon
Gly[9] Ile[26] glucagon
des Thr[5] des Asp[9] glucagon
---

Compounds within the scope of the invention also include those from which the histidine residue at the one position, i.e. the amino terminal has been removed. Typical of such compounds are:

---
des - His[1] [Lys[9]] glucagon,
des - His[1] [Gly[9]] glucagon,
des - His[1] [Nle[9]] glucagon
and the carboxyl terminal amides of such compounds.
---

In fact, compounds such as the above, including the amides, from which the amino terminal histidine has been removed comprise the preferred compounds of this invention because they presently appear to have the best therapeutic properties.

The products of this invention were synthesized by known solid phase techniques. See, for example, Barany and Merrifield (1979) in *The Peptides*, eds. Gross and Meienhofer (Academic Press, New York) Vol. 2A, pages 1 to 284. The products can be prepared by manual methods or, for example, on a peptide synthesizer such as the Applied Biosystems 430 unit.

Analogs with a free C-terminal carboxyl were made on phenylacetamidomethyl-resin supports, and those with C-terminal amides were made on a methylbenzhydrylamine-resin. Side chain protection was Arg(Tos), Asp(OcHx), Glu(OcHx), His(Tos), Lys(ClZ), Ser(Bzl), Thr(Bzl), Trp(For), and Tyr(BrZ). Double couplings with preformed symmetric anhydrides in dimethylformamide were used routinely for all tert-butyloxycarbonyl-protected amino acids except for tosyl arginine, glutamine, and asparagine, where N-hydroxybenzo triazole esters in dimethylformamide were required [Konig, W. & Geiger, R. Chem. Ber. 103, 788 (1970)]. The assembled protected peptide-resins were cleaved by the "low/high HF" technique [Tam, J. P., Heath, W. F. & Merrifield, R. B. J. Am. Chem. Soc. 105, 6442 (1983)], which was developed to avoid a number of potential side reactions. After evaporation of HF and washing with ether, the crude free peptide was extracted with 10% acetic acid and lyophilized. Purification of the synthetic peptides was performed by preparative low-pressure reverse-phase liquid chromatography on $C_{18}$-silica as described [Andreu, D. & Merrifield, R. B. in Peptides: Structure and Function, eds. Deber, C. M., Hruby, V. J. & Kopple, K. D. (Pierce Chem. Co., Rockford, Ill.), pp. 595–598. The overall yields were between 35 and 40%. Homogeneity was demonstrated by analytical HPLC, and identity was confirmed by amino acid analysis, mass spectroscopy and molecular weight determinations.

The amino acid analysis of all compounds prepared agreed with theory within ±5%, and the molecular weights determined by mass spectrometry were within 0.5 mass units.

Tert-Butyloxycarbonyl (Boc) protected amino acids were from Peninsula Laboratories, (San Carlos, (A.) p-methylbenzhydrylamine resin (0.45 mmol/g) was from United States Biochemical (Cleveland, Ohio) and Boc-Thr-(Bzl)-4-oxymethylphenylacetamidomethyl copoly (styrene-1% divinyl benzene) was prepared as described by Mitchell et al, J. Org. Chem. 43, 2845 (1978).

$^{125}$I-labeled glucagon from New England Nuclear was used without further purification for periods up to 1 month after its preparation. Creatine phosphate, creatine kinase, bovine serum albumin, dithiothreitol, GTP, and ATP were from Sigma. A cAMP assay kit containing [8-$^3$H]cAMP was from Amersham. Nuflow membrane filters (0.45 um) were from Oxoid (Basingstoke, England).

Various tests were employed to determine the efficacy of the products of this invention. These included the membrane binding assay and adenyl cyclase assays.

Membrane Binding Assay. Liver plasma membranes were prepared from male Sprague-Dawley rats (Charles River Breeding Laboratories) by the Neville procedure as described by Pohl [Pohl, S. L. (1976) in Methods in Receptor Research, ed. Blecher, M. (Marcel Dekker, New York), pp. 160–164]. The receptor binding assay was as described by Wright and Rodbell [Wright, D. E. & Rodbell, M. (1979) J. Biol. Chem. 254, 268–269] in which competition for glucagon receptors between $^{125}$I-labeled natural glucagon (1.6 nM) and the unlabeled synthetic analog was measured. After correction for the blank, the percentage of displacement of label was compared with that of a purified glucagon standard, and the relative binding affinity was calculated.

Adenylate Cyclase Assay. The assay on liver membranes was performed according to Salomon et al. [Salomon, Y., Londos, C. & Rodbell, M. Anal. Biochem. 58, 541, 548 (1974)]. The released cAMP was mixed with [8-$^3$H]cAMP measured with a high affinity cAMP binding protein.

The purpose of the membrane binding assay is to measure the ability of analogs of glucagon to bind to liver membrane protein compared to that of glucagon.

When the glucagon analogs of this invention were assayed, they were assayed as amides with natural glucagon amide as a standard, thus eliminating the possibility of imprecision due to the heterogeneity of membrane preparations. In fact, it presently appears that C-terminal amides are more active than the corresponding carboxyl compounds. Accordingly, C-terminal amides of the glucon analogs of the invention are the presently preferred compounds of the invention.

The relative binding affinity of a given analog is expressed as:

$$\frac{\text{(half maximal displacement concentration of glucagon)}}{\text{(half maximal displacement concentration of analog)}} \times 100$$

The purpose of the adenylate cyclase assay is to measure the ability of the compound under test to stimulate the activity of adenylate cyclase. The assays are used to measure relative potency, maximum activity and inhibition index.

The inhibition index, defined above, was determined from adenylate cyclase assays by two different protocols.

1. A glucagon standard curve for cAMP vs glucagon concentration was established. Then another glucagon assay curve was measured in the presence of a constant amount of antagonist. The concentration of glucagon that had its activity reduced to 50% by that concentration of inhibitor was then determined.

2. A series of tubes were set up containing an amount of glucagon which will produce 90% of maximum response. Increasing amounts of antagonist were then added and the concentration that reduced the response to 45% of maximum was determined.

Since normal circulating levels of glucagon are about $10^{-10}$ molar, a product with an inhibition index of 12 would only need to be present in vivo at a concentration of 0.4 ug/ml of blood to inhibit completely the action of glucagon. The compounds of this invention have an inhibition index up to about 150, but preferably up to about 10, coupled with a membrane binding activity of at least 10%. It is much preferred that the inhibition index be 12 or less, and that the relative binding affinity be at least 10%.

In the most preferred compounds of this invention the $pA_2$ value is at least 5 and preferably above 7.

The $pA_2$ value is the negative logarithm of the concentration of antagonist that reduces the response to 1 unit of agonist to the response obtained from 0.5 unit of agonist.

The following table shows the results of measurements with glucagon and certain of the compounds of this invention measured as amides.

TABLE 1

| Glucagon amide | % Binding Affinity | % Maximum Activity | % Relative Activity | Inhibition Index, I/A50 | pA$_2$ Value |
|---|---|---|---|---|---|
| 1. glucagon amide | 100 | 100 | 15 | — | — |
| 2. D-Asp$^9$ | 1.62 | 0 | <0.0044 | 129 | 5.2 |
| 3. des-Asp$^9$ | 45 | 8.3 | 1.04 | 5.2 | 7.2 |
| 4. Glu$^9$-(OCH$_3$) | 100 | 50 | 0.05 | 10 | 8.65 |
| 5. Asn$^9$ | 42 | 33 | 0.17 | 24.5 | 6.0 |
| 6. Lys$^9$ | 54 | 0 | <0.0055 | 30 | 6.4 |
| 7. Nle$^9$ | 32 | 21.8 | 0.17 | 4 | 7.7 |
| 8. Asp$^1$His$^9$ | 24 | 0 | <0.0009 | 31 | 6.3 |
| 9. des-His$^1$[D-Asp$^9$] | 3.6 | 0 | <0.0028 | 97.5 | 5.9 |
| 10. des-His$^1$[D-Glu$^9$] | 16 | 0 | <0.0037 | 69 | 5.4 |
| 11. des-His$^1$[Glu$^9$-(OCH$_3$)] | 66 | 13 | 0.011 | 8.7 | 7.35 |
| 12. des-His$^1$[Asn$^9$] | 52.3 | 0 | <0.0026 | 24.5 | 6.52 |
| 13. des-His$^1$[Gln$^9$] | 33 | 0 | <0.003 | 8.3 | 8.21 |
| 14. des-His$^1$[Gly$^9$] | 100 | 0 | <0.006 | 43 | 6.24 |
| 15. des-His$^1$[Lys$^9$] | 70 | 0 | <0.0012 | 5 | 7.35 |
| 16. des-His$^1$[His$^9$] | 35 | 6 | 0.011 | 8.7 | 7.0 |
| 17. des-His$^1$[Nle$^9$] | 125 | 0 | <0.0012 | 19 | 7.6 |
| 18. des-His$^1$[Phe$^9$] | 11 | 0 | <0.0003 | 27 | 6.2 |
| 19. des-His$^1$des-Asp$^9$ | 7 | 0 | <0.0022 | 77 | 5.5 |

The presently preferred compounds within the scope of this invention are:

des—His$^1$ [Gly$^9$] glucagon amide
des—His$^1$ [Nle$^9$] glucagon amide
des—His$^1$ [Lys$^9$] glucagon amide The glucagon analogs of this invention also include derivatives having the defined properties. As indicated above, C-terminal amides are actually preferred over the C-terminal carboxyl comopunds. Side chain amides such as amides of dibasic acids are also useful. Esters, especially those based on alkyl or aralkyl alcohols corresponding to the amides may also be employed. Ethers, especially lower alkyl ethers of analogs including Ser, Thr and Tyr amino acid residues are also useful, as are esters of these analogs based on alkyl, aryl and aralkyl acids. Glucagon analogs containing amino acid residues with additional functional group may also be converted to derivatives within the scope of the inveniton. These might inlcude, for example N-acetyl derivatives of di-amino acids such as lysine.

One class of useful derivatives is based on des-His$^1$ glucagon analogs in which the hydroxyl group of the amino terminal serine residue has been converted to a 2, 4 - difluorobenzoyl ester. Other hydroxyl and amine substituted amino acids derivatized with 2, 4- difluorobenzoic acid are within the scope of the invention whether or not the histadyl residue at the 1-position is in place.

In some instances, compounds within the scope of the invention may be synthesized and thereafter utilized with one or more of the blocking groups still in place.

The products of this invention will generally be administered in the same manner as insulin, i.e. parenterally or by infusion. Since their chemical structure and activity is quite similar to insulin they will generally be administered with the same types of pharmaceutically acceptable excipients as insulin. They may in fact be coadministered with insulin in the same dosage units. They may also be administered simultaneously with the insulin although not in the same composition.

Since the products of the invention are amphoteric they may be utilized as free bases, as acid addition salts or as metal salts. The salts must, of course, be pharmaceutically acceptable, and these will include metal salts particularly alkali and alkaline earth metal salts, suitably potassium or sodium salts. A wide variety of pharmaceutically acceptable acid addition salts are available. These include those prepared from both organic and inorganic acids, preferably mineral acids. Typical acids which may be mentioned by way of example include citric, succinic, lactic, hydrochloric and hydrobromic acids. Such products are readily prepared by procedures well known to those skilled in the art.

The products of the invention will normally be provided for as parenteral compositions for injection or infusion. They can, for example be suspended in an inert oil, suitably a vegetable oil such as sesame, peanut, or olive oil. Alternatively they can be suspended in an aqueous isotonic buffer solution at a pH of about 5.6 to 7.4. Useful buffers include sodium citrate-citric acid and sodium phosphate-phosphoric acid.

The desired isotonicity may be accomplished using sodium chloride or other pharmaceutically acceptable agents such as dextrose, boric acid, sodium tartrate, propylene glycol or other inorganic or organic solutes. Sodium chloride is preferred particularly when the buffer contains sodium ions.

If desired the solutions may be thickened with a thickening agent such as methyl cellulose. They may be prepared in emulsified form, either water in oil or oil in water. Any of a wide variety of pharmaceutically acceptable emulsifying agents may be employed including, for example acacia powder, or an alkaryl polyether alcohol sulfate or sulfonate such as a Triton.

The therapeutically useful compositions of the invention are prepared by mixing the ingredients following generally accepted procedures. For example, the selected components may be simply mixed in a blender or other standard device to produce a concentrated mixture which may then be adjusted to the final concentration and viscosity by the addition of water or thickening agent and possibly a buffer to control pH or an additional solute to control tonicity.

For use by the physician, the compositions will be provided in dosage unit form containing an amount of glucagon analog which will be effective in one or multiple doses to control glucogenesis or blood sugar at the selected level, normally in the presence of insulin. As will be recognized by those skilled in the art, an effective amount of the therapeutic agent will vary with many factors including the age and weight of the patient, the amount of insulin which is concurrently employed, the blood sugar level to be obtained, the inhibition index of the selected analog, and other factors. Typical dosage units will contain from 0.2 to 0.8 ug/ml although wide variations from this range are possible while yet achieving useful results.

What is claimed is:

1. Glucagon analogs characterized by the removal of the L-aspartic acid residue at the 9-position or its replacement with an amino acid residue other than an L-dibasic amino acid containing up to 5 carbon atoms and by a relative binding activity of at least about 10% and an inhibition index up to about 150, or a pharmaceutically acceptable acid addition salt thereof.

2. A des-His$^1$-glucagon analog of claim 1, or a pharmaceutically acceptable acid addition salt thereof.

3. A des-His$^1$-[Gly$^9$] glucagon analog of claim 1, or a pharmaceutically acceptable acid addition salt thereof.

4. A des-His$^1$-[Nle$^9$] glucagon analog of claim 1, or a pharmaceutically acceptable acid addition salt thereof.

5. A des-His$^1$−[Lys$^9$] glucagon analog of claim 1, or a pharmaceutically acceptable acid addition salt thereof.

6. des-His$^1$ [Gly$^9$] glucagon amide.

7. des-His$^1$ [Nle$^9$] glucagon amide.

8. des-His$^1$ [Lys$^9$]-glucagon amide.

9. A parenteral composition for the control of glucogenesis in humans containing a pharmaceutically acceptable carrier and a pharmaceutically acceptable amount of a glucagon analog characterized by the removal of the L-aspartic acid residue at the 9-position or its replacement with an amino acid residue other than an L- dibasic amino acid containing up to 5 carbon atoms and by a relative binding activity of at least about 10% and an inhibition index up to about 150 or a pharmaceutically acceptable acid addition salt thereof.

10. A parenteral composition of claim 9 wherein the glucagon analog is a des-His$^1$-glucagon, or a pharmaceutically acceptable acid addition salt thereof.

11. A parenteral composition of claim 9 wherein the glucagon analog is des-His$^1$-[Gly$^9$] glucagon, or a pharmaceutically acceptable acid addition salt thereof.

12. A parenteral composition of claim 9 wherein the glucagon analog is des-His$^1$-[Nle$^9$] glucagon, or a pharmaceutically acceptable acid addition salt thereof.

13. A parenteral composition of claim 9 wherein the glucagon analog is des-His$^1$-[Lys$^9$] glucagon, or a pharmaceutically acceptable acid addition salt thereof.

14. A parenteral composition in dosage unit form for the control of glucogenesis in humans containing a pharmaceutically acceptable carrier and from about 0.2 to 0.8 ug/ml of a glucagon analog characterized by the removal of the L-aspartic acid residue at the 9- position or its replacement with an amino acid residue other than an L- dibasic amino acid containing up to 5 carbon atoms and by a relative binding activity of at least about 10% and an inhibition index up to about 150 or a pharmaceutically acceptable acid addition salt thereof.

15. A parenteral composition in dosage unit form of claim 14 wherein the glucagon analog is des-His$^1$-glucagon, or a pharmaceutically acceptable acid addition salt thereof.

16. A parenteral composition in dosage unit form of claim 14 wherein the glucagon analog is des-His$^1$-[Gly$^9$] glucagon, or a pharmaceutically acceptable acid addition salt thereof.

17. A parenteral composition in dosage unit form of claim 14 wherein the glucagon analog is des-His$^1$-[Nle$^9$] glucagon, or a pharmaceutically acceptable acid addition salt thereof.

18. A parenteral composition in dosage unit form of claim 14 wherein the glucagon analog is des-His$^1$-[Lys$^9$] glucagon, or a pharmaceutically acceptable acid addition salt thereof.

* * * * *